United States Patent
Sadaka (10) Patent No.: US 8,523,778 B2
(45) Date of Patent: Sep. 3, 2013

(54) SYSTEMS AND METHODS FOR FLUSHING AIR FROM A CATHETER OF AN INTRAVASCULAR ULTRASOUND IMAGING SYSTEM

(75) Inventor: Alain Sadaka, San Jose, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 526 days.

(21) Appl. No.: 12/945,053

(22) Filed: Nov. 12, 2010

(65) Prior Publication Data

US 2011/0125027 A1 May 26, 2011

Related U.S. Application Data (60) Provisional application No. 61/264,451, filed on Nov. 25, 2009.

(51) Int. Cl.
*A61B 8/00* (2006.01)
(52) U.S. Cl.
USPC ........... 600/467; 600/407; 600/443; 600/438; 600/439; 600/463
(58) Field of Classification Search
USPC ............... 600/407, 437, 443, 438, 467, 463, 600/476, 466, 549
See application file for complete search history.

(56) References Cited

U.S. PATENT DOCUMENTS

| | | | | |
|---|---|---|---|---|
| 5,375,602 A | * | 12/1994 | Lancee et al. | 600/463 |
| 6,945,938 B2 | | 9/2005 | Grunwald | |
| 7,037,271 B2 | * | 5/2006 | Crowley | 600/463 |
| 7,306,561 B2 | | 12/2007 | Sathyanarayana | |
| 2006/0100522 A1 | | 5/2006 | Yuan et al. | |
| 2006/0173350 A1 | | 8/2006 | Yuan et al. | |
| 2006/0253028 A1 | | 11/2006 | Lam et al. | |
| 2007/0016054 A1 | | 1/2007 | Cao et al. | |
| 2007/0038111 A1 | | 2/2007 | Rehig et al. | |
| 2010/0249603 A1 | * | 9/2010 | Hastings et al. | 600/467 |
| 2011/0071400 A1 | * | 3/2011 | Hastings et al. | 600/467 |

* cited by examiner

*Primary Examiner* — Joel Lamprecht
(74) *Attorney, Agent, or Firm* — Frommer Lawrence & Haug LLP; Patrick R. Turner (57) ABSTRACT

A catheter assembly for an intravascular ultrasound system includes a hub disposed at a proximal end of a catheter. The hub includes a rotatable connector shaft disposed at least partially in a lumen that extends from the hub to a distal end of the catheter. A pumping apparatus is coupled to the connector shaft such that rotation of the connector shaft causes a corresponding rotation of the pumping apparatus. A reservoir is in fluid communication with the pumping apparatus. The reservoir is configured and arranged for inputting an acoustically-favorable medium to the pumping apparatus. An imaging core is configured and arranged for inserting into the lumen. The imaging core includes an imaging device coupled to a rotatable drive member. The rotatable connector shaft is coupled to a proximal end of the drive member such that rotation of the connector shaft causes a corresponding rotation of the imaging core.

20 Claims, 7 Drawing Sheets

SYSTEMS AND METHODS FOR FLUSHING AIR FROM A CATHETER OF AN INTRAVASCULAR ULTRASOUND IMAGING SYSTEM

CROSS-REFERENCE TO RELATED APPLICATIONS

This application claims the benefit under 35 U.S.C. §119(e) of U.S. Provisional Patent Application Ser. No. 61/264,451 filed on Nov. 25, 2009, which is incorporated herein by reference.

TECHNICAL FIELD

The present invention is directed to the area of intravascular ultrasound imaging systems and methods of making and using the systems. The present invention is also directed to an intravascular ultrasound imaging system with a pumping apparatus for flushing air from a lumen of a catheter, as well as methods of making and using the intravascular ultrasound systems, catheter, and pumping apparatus.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include, for example, a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiment, a catheter assembly for an intravascular ultrasound system includes an elongated catheter having a distal end and a proximal end. The catheter defines a lumen extending along the catheter from the proximal end to the distal end. The catheter includes a hub disposed at the proximal end of the catheter. The hub includes a rotatable connector shaft disposed at least partially in the lumen. A pumping apparatus is coupled to the connector shaft such that rotation of the connector shaft causes a corresponding rotation of the pumping apparatus. A reservoir is in fluid communication with the pumping apparatus. The reservoir is configured and arranged for inputting an acoustically-favorable medium to the pumping apparatus. An imaging core is configured and arranged for inserting into the lumen. The imaging core includes an imaging device coupled to a distal end of an elongated, rotatable drive member. The imaging device includes at least one transducer mounted to the imaging device. The at least one transducer is configured and arranged for transforming applied electrical signals to acoustic signals and also for transforming received echo signals to electrical signals. The rotatable connector shaft is coupled to a proximal end of the drive member such that rotation of the connector shaft causes a corresponding rotation of the imaging core.

In another embodiment, a catheter assembly for an intravascular ultrasound system includes an elongated catheter having a distal end and a proximal end. The catheter defines a lumen extending along the catheter from the proximal end to the distal end. The catheter includes a hub disposed at the proximal end of the catheter. The hub includes a rotatable connector shaft at least partially disposed in the lumen. A pumping apparatus is coupleable to the connector shaft. Rotation of the connector shaft causes a corresponding rotation of the pumping apparatus when the pumping apparatus is coupled to the connector shaft. A reservoir is in fluid communication with the pumping apparatus. The reservoir is configured and arranged for inputting an acoustically-favorable medium to the pumping apparatus. An imaging core is configured and arranged for inserting into the lumen. The imaging core includes an imaging device coupled to a distal end of an elongated, rotatable drive member. The imaging device includes at least one transducer mounted to the imaging device. The at least one transducer is configured and arranged for transforming applied electrical signals to acoustic signals and also for transforming received echo signals to electrical signals. The rotatable connector shaft is coupled to a proximal end of the drive member such that rotation of the connector shaft causes a corresponding rotation of the imaging core.

In yet another embodiment, a method for flushing air from a catheter of an intravascular ultrasound imaging system includes inserting a distal end of a catheter into a patient. The catheter defines a lumen extending along the catheter from a proximal end to a distal end. The catheter includes a hub disposed at the proximal end of the catheter. The hub includes a rotatable connector shaft disposed in the lumen and a pumping apparatus. An imaging core is inserted into the lumen. The imaging core includes an imaging device coupled to a distal end of an elongated, rotatable drive member. The imaging device includes at least one transducer mounted to the imaging device. The drive member is coupled to the connector shaft. Acoustically-favorable medium is provided to the pumping apparatus from a reservoir in fluid communication with the lumen. The connector shaft is rotated to cause a corresponding rotation of the imaging core. The pumping apparatus is coupled to the connector shaft to cause the pumping apparatus to rotate with the connector shaft. The acoustically-favorable medium is pumped from the hub to the imaging device using the pumping apparatus.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound imaging systems and methods of making and using the systems. The present invention is also directed to an intravascular ultrasound imaging system with a pumping apparatus for flushing air from a lumen of a catheter, as well as methods of making and using the intravascular ultrasound systems, catheter, and pumping apparatus.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
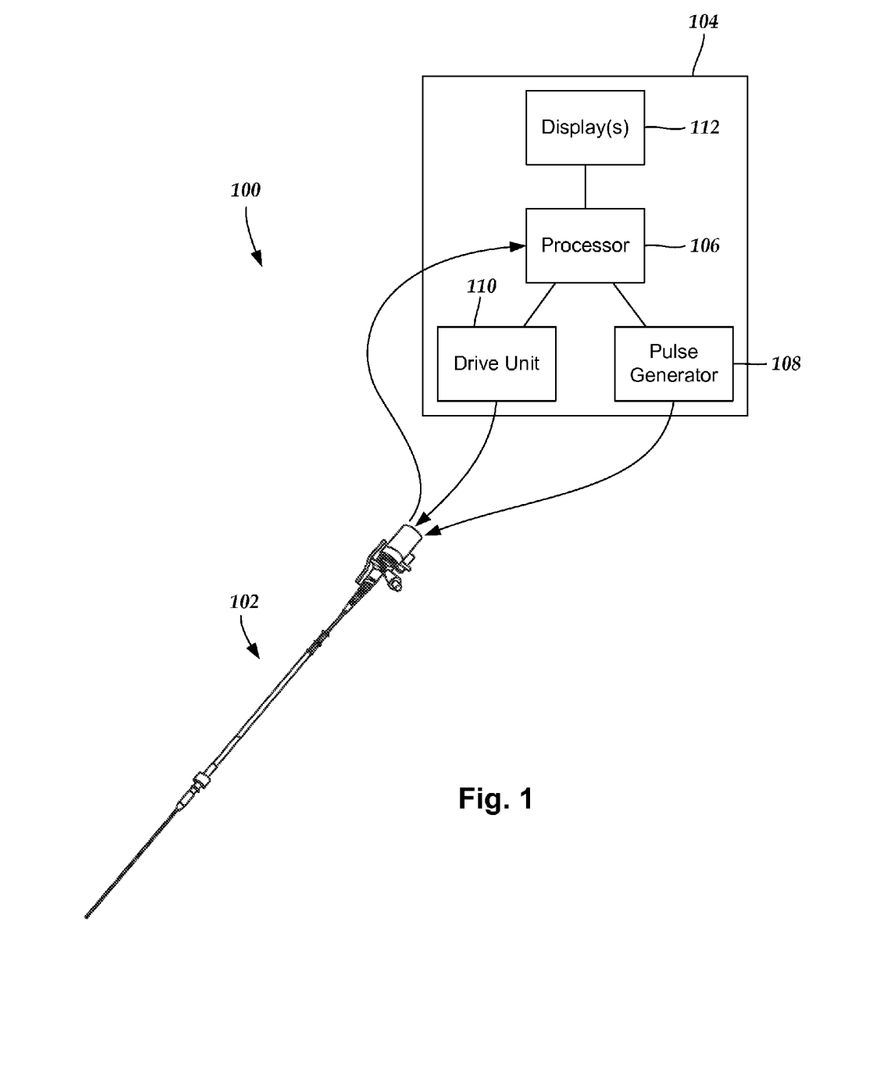
FIG. 1 is a schematic view of one embodiment of an intravascular ultrasound imaging system, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric signals that may be input to one or more transducers (312 in FIG. 3) disposed in the catheter 102. In at least some embodiments, mechanical energy from the drive unit 110 may be used to drive an imaging core (306 in FIG. 3) disposed in the catheter 102. In at least some embodiments, electric signals transmitted from the one or more transducers (312 in FIG. 3) may be input to the processor 106 for processing. In at least some embodiments, the processed electric signals from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical signals transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
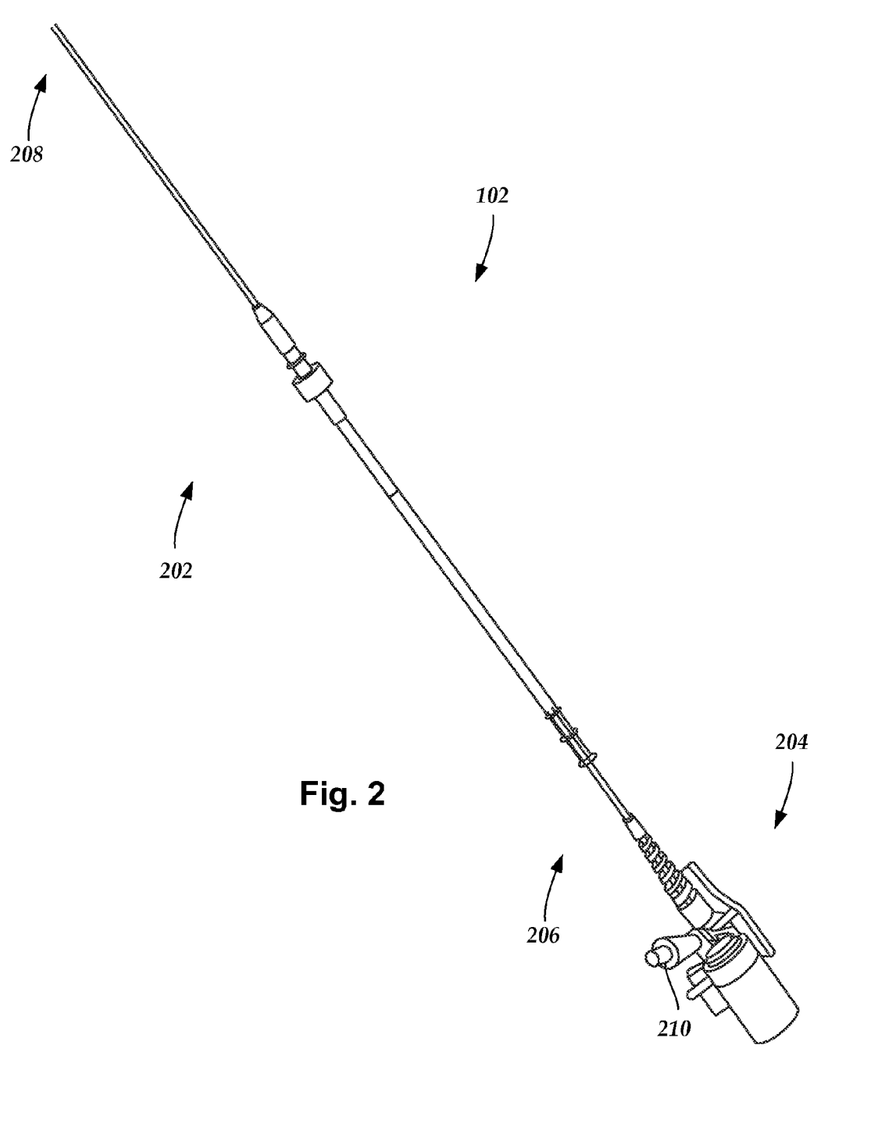
FIG. 2 is a schematic side view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
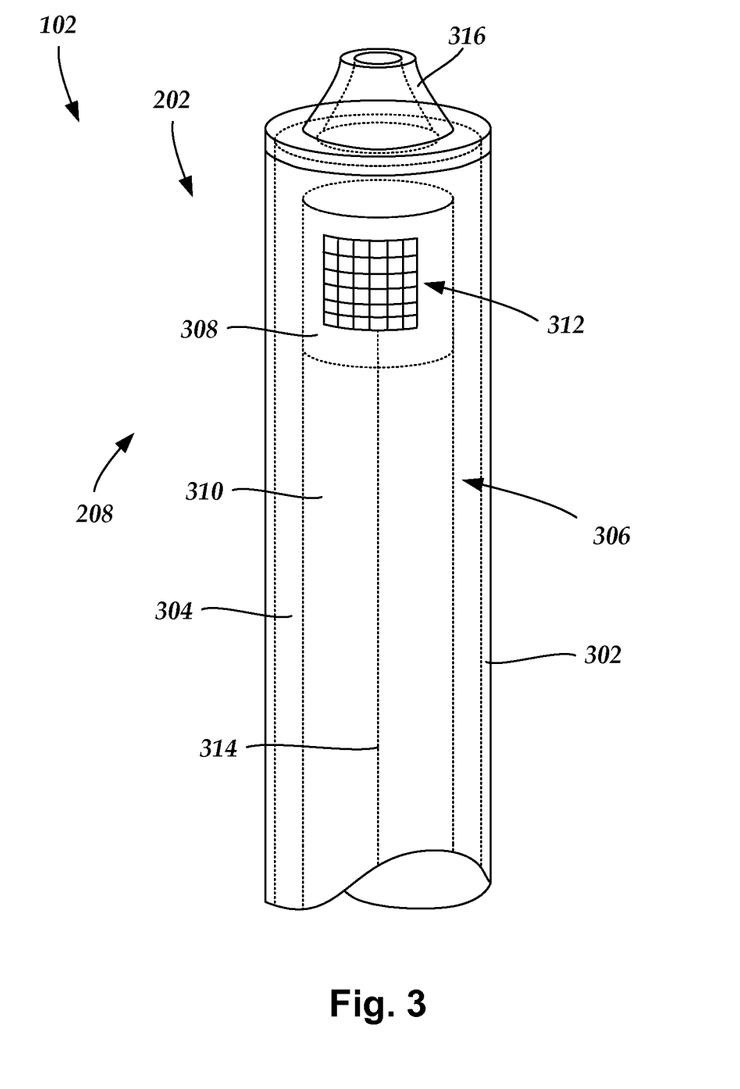
FIG. 3 is a schematic perspective view of one embodiment of a distal end of the catheter shown in FIG. 2 with an imaging core disposed in a lumen defined in the catheter, according to the invention.

FIG. 3 is a schematic perspective view of one embodiment of the distal end 208 of the elongated member 202 of the catheter 102. The elongated member 202 includes a sheath 302 and a lumen 304. An imaging core 306 is disposed in the lumen 304. The imaging core 306 includes an imaging device 308 coupled to a distal end of a drive member 310 (e.g., one or more cables, elongated conductive devices, or the like).

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device 308 and employed to transmit and receive acoustic signals. In a preferred embodiment (as shown in FIG. 3), an array of transducers 312 are mounted to the imaging device 308. In other embodiments, a single transducer may be employed. In yet other embodiments, multiple transducers in an irregular-array may be employed. Any number of transducers 312 can be used. For example, there can be one, two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical signals to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic signals of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic signals of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic signals.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form a composite image of the walls of the blood vessel and tissue surrounding the blood vessel by stitching together a plurality of individual image frames.

In at least some embodiments, the imaging core 306 may be rotated about a longitudinal axis of the catheter 102. As the imaging core 306 rotates, the one or more transducers 312 emit acoustic signal in different radial directions. When an emitted acoustic signal with sufficient energy encounters one or more medium boundaries, such as one or more tissue boundaries, a portion of the emitted acoustic signal is reflected back to the emitting transducer as an echo signal. Each echo signal that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to generate a displayable image frame of the imaged region based, at least in part, on a collection of information from each of the acoustic signals transmitted and the echo signals received. In at least some embodiments, the rotation of the imaging core 306 is driven by the drive unit 110 disposed in the control module (104 in FIG. 1) via a connector shaft (404 in FIG. 4) in the hub 204 and the drive member 310 extending along the elongated member 202 of the catheter 102.

As the one or more transducers 312 rotate about the longitudinal axis of the catheter 102 emitting acoustic signals, a plurality of image frames are formed that collectively form a composite radial cross-sectional image of a portion of the region surrounding the one or more transducers 312, such as the walls of a blood vessel of interest and the tissue surrounding the blood vessel. In at least some embodiments, one or more of the image frames can be displayed on the one or more displays 112. In at least some embodiments, the radial cross-sectional composite image can be displayed on the one or more displays 112.

In at least some embodiments, the imaging core 306 may also move longitudinally along the blood vessel within which the catheter 102 is inserted so that a plurality of composite cross-sectional images may be formed into one or more larger composite images that include an axial length of the blood vessel. In at least some embodiments, during an imaging procedure the one or more transducers 312 may be retracted (i.e., pulled back) along the longitudinal length of the catheter 102. In at least some embodiments, the catheter 102 includes at least one section that can be retracted during pullback of the one or more transducers 312. In at least some embodiments, the drive unit 110 drives the pullback of the imaging core 306 within the catheter 102. In at least some embodiments, the drive unit 110 pullback distance of the imaging core is at least 5 cm. In at least some embodiments, the drive unit 110 pullback distance of the imaging core is at least 10 cm. In at least some embodiments, the drive unit 110 pullback distance of the imaging core is at least 15 cm. In at least some embodiments, the drive unit 110 pullback distance of the imaging core is at least 20 cm. In at least some embodiments, the drive unit 110 pullback distance of the imaging core is at least 25 cm. In at least some embodiments, the catheter 102 pullback occurs along one or more telescoping sections.

The quality of imaging at different depths from the one or more transducers 312 may be affected by one or more factors including, for example, bandwidth, transducer focus, beam pattern, as well as the frequency of the acoustic signal. The frequency of the acoustic signal output from the one or more transducers 312 may also affect the penetration depth of the acoustic signal output from the one or more transducers 312. In general, as the frequency of an acoustic signal is lowered, the depth of the penetration of the acoustic signal within patient tissue increases. In at least some embodiments, the IVUS imaging system 100 operates within a frequency range of 5 MHz to 60 MHz.

In at least some embodiments, one or more transducer conductors 314 electrically couple the transducers 312 to the control module 104 (See FIG. 1). In at least some embodiments, the one or more transducer conductors 314 extend along the drive member 310.

In at least some embodiments, one or more transducers 312 may be mounted to the distal end 208 of the imaging device 308. The imaging device 308 may be inserted in the lumen of the catheter 102. In at least some embodiments, the catheter 102 (and imaging device 308) may be inserted percutaneously into a patient via an accessible blood vessel, such as the femoral artery, at a site remote from a target imaging location. The catheter 102 may then be advanced through patient vasculature to the target imaging location, such as a portion of a selected blood vessel.

Acoustic signals propagating from the one or more transducers 312 propagate through a portion of the lumen 304 surrounding the imaging device 308 before passing through the sheath 302 to the region exterior of the catheter 102, such as a blood vessel or a chamber of a heart. Likewise, echo signals reflected back to the one or more transducers 312 from medium boundaries also propagate through a portion of the lumen 304. Typically, air is not a desirable transmission medium and image quality may, consequently, be reduced when acoustic signals or echo signals are required by catheter design to propagate through air. In the MHz range, acoustic signals may not propagate at all through air. Accordingly, it is typically advantageous, and in some cases necessary, to purge air from the lumen 304 surrounding the one or more transducers 312 prior to (or one or more times during) the performance of an imaging procedure.

One technique for purging air surrounding the one or more transducers 312 is to flush the lumen 304 with an acoustically-favorable medium through which acoustic signals more easily propagate than through air Acoustically-favorable media may include one or more solvents such as, for example, water. An acoustically-favorable medium may include one or more solutes mixed with the one or more solvents such as, for example, one or more salts. In at least some embodiments, one or more agents may also be added, for example, to decrease the potential advancement of corrosion or microbial growth. In at least some embodiments, an acoustically-favorable medium may include a gel, and the like. In at least some embodiments, the acoustically-favorable medium may be input through one or more flush ports, such as the flush port 210. In at least some embodiments, the elongated member 202 also defines an output port 316 in fluid communication with the lumen 304 for outputting one or more gases.

When using a conventional IVUS imaging system, a lumen of a catheter may be manually flushed to remove air at the beginning of an IVUS imaging procedure. Additionally, the lumen of the catheter may also be manually flushed of air one or more additional times during the course of the IVUS imaging procedure. Unfortunately, each manual flushing of air from the catheter lumen can add to the amount of time it takes to perform an IVUS imaging procedure on a patient.

A rotatable pumping apparatus ("pumping apparatus") can be used to flush air from the lumen. In at least some embodiments, the pumping apparatus is configured and arranged to rotate with the imaging core 306. In at least some embodiments, the pumping apparatus includes a screw pump, or Archimedes's screw. In some embodiments, the pumping apparatus rotates whenever the imaging core 306 rotates. In other embodiments, the pumping apparatus is configured and arranged such that the pumping apparatus is transitioned between an engaged position, where the pumping apparatus rotates with the imaging core 306, and a disengaged position, where the pumping apparatus does not rotate with the imaging core 306.

In at least some embodiments, the pumping apparatus enables air to be flushed from the lumen and replaced by an acoustically-favorable medium. In at least some embodiments, the pumping apparatus enables air to be flushed from the lumen prior to an IVUS imaging procedure. In at least some embodiments, the pumping apparatus enables air to be flushed from the lumen at least one time during an IVUS imaging procedure. In at least some embodiments, the acoustically-favorable medium is supplied to the pumping apparatus via a reservoir in fluid communication with the pumping apparatus.

In at least some embodiments, the pumping apparatus is disposed in the hub 204. In at least some embodiments, the lumen 304 of the catheter 102 extends within a portion of the hub 204. In at least some embodiments, the pumping apparatus is disposed in the hub 204 such that the pumping apparatus is in fluid communication with the lumen 304 of the catheter 102. In at least some embodiments, the pumping apparatus is disposed in the hub 204 such that the pumping apparatus is also disposed in the lumen 304.

In at least some embodiments, the hub 204 includes a connector shaft (404 in FIG. 4) coupled to the drive unit 110. In at least some embodiments, the connector shaft couples the drive unit 110 to the imaging device 308 via the drive member 310. In at least some embodiments, the pumping apparatus is coupled to the connector shaft. In at least some embodiments the pumping apparatus is coupled directly to the connector shaft. In at least some embodiments the pumping apparatus is coupled indirectly to the connector shaft. In at least some embodiments, the pumping apparatus is at least partially disposed over at least a portion of the connector shaft. In at least some embodiments, the pumping apparatus is coupleable to the connector shaft. In at least some embodiments, the pumping apparatus is configured and arranged to be selectively coupled and uncoupled with the connector shaft.

Figure 4:
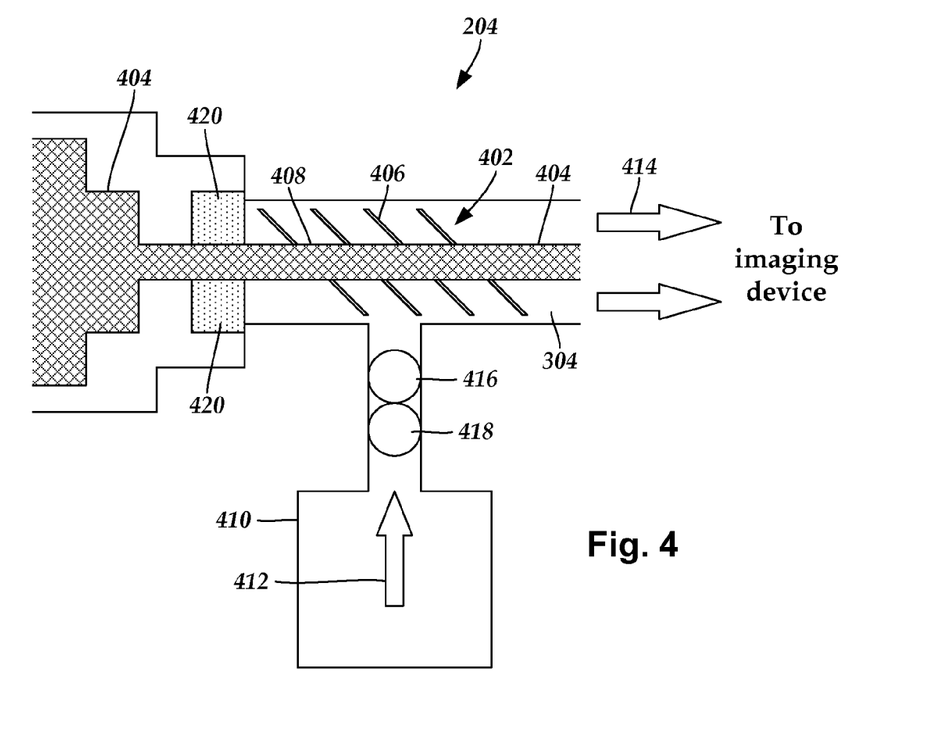
FIG. 4 is a schematic longitudinal cross-sectional view of one embodiment of a pumping apparatus disposed in a hub of a catheter such that rotation of a connector shaft causes a corresponding rotation of the pumping apparatus, according to the invention.

FIG. 4 is a schematic longitudinal cross-sectional view of one embodiment of a pumping apparatus 402 disposed in the hub 204 of the catheter 102. The pumping apparatus 402 is disposed in the lumen 304 such that the pumping apparatus 402 is in fluid communication with the imaging device 308. The hub 204 also includes a connector shaft 404. In at least some embodiments, the pumping apparatus 402 includes a screw pump that includes one or more blades 406 that rotate about an axle 408. In at least some embodiments, the pumping apparatus 402 is coupled to the connector shaft 404 such that rotation of the connector shaft 404 causes a corresponding rotation of the pumping apparatus 402. In at least some embodiments, the axle 408 of the pumping apparatus 402 is affixed (e.g., using an adhesive, interference fit, or the like) to the connector shaft 404. In at least some embodiments, the pumping apparatus 402 and the connector shaft 404 are inseparable from one another. In at least some embodiments, the pumping apparatus 402 and the connector shaft 404 are formed from a single piece of material (i.e., a unitary structure).

A reservoir 420 is coupled to the catheter 102. In at least some embodiments, the reservoir 420 is coupled to the hub 204. In at least some embodiments, the reservoir 420 is in fluid communication with the lumen 304. In at least some embodiments, the reservoir 420 is in fluid communication with the pumping apparatus 402. In at least some embodiments, the reservoir 420 is coupled to the catheter 102 via the flush port 210. In at least some embodiments, the reservoir 410 is permanently coupled to the catheter 102. In at least some embodiments, the reservoir 410 is removably coupled to the catheter 102. In at least some embodiments, a plurality of reservoirs are coupled to the catheter 102.

In at least some embodiments, the reservoir 410 is at least partially filled with the acoustically-favorable medium. In at least some embodiments, the reservoir 410 is configured and arranged to output the acoustically-favorable medium to the pumping apparatus 402, as shown by arrow 412. In at least some embodiments, the reservoir 410 continuously outputs the acoustically-favorable medium from the reservoir 410. In at least some embodiments, the reservoir 410 intermittently outputs the acoustically-favorable medium from the reservoir 410. In at least some embodiments, the rate of output of the acoustically-favorable medium from the reservoir 410 is user-controlled. In at least some embodiments, the rate of output of the acoustically-favorable medium from the reservoir 410 is preset.

During operation, the pumping apparatus 402 is configured and arranged to pump the acoustically-favorable medium to the imaging device 308, as shown by arrows 414. The amount of the acoustically-favorable medium pumped to the imaging device 308 may be affected by many different factors including, for example, the amount of acoustically-favorable fluid pumped from the reservoir 410 to the pumping apparatus 402, the rotational velocity of the pumping apparatus 402, the size and shape of the blades 406, the amount of clearance between the blades 406 and inner walls of the lumen 304, or the like or combinations thereof.

In at least some embodiments, one or more check valves 416 are disposed between the lumen 304 and the reservoir 410 to prevent the acoustically-favorable medium from passing from the lumen 304 to the reservoir 410. In at least some embodiments, a shut-off valve 418 is disposed between the one or more check valves 416 and the reservoir 410. The shut-off valve 418 is configured and arranged for shutting off the flow of the acoustically-favorable medium from the reservoir 410 to the pumping apparatus 402. In at least some embodiments, the shut-off valve 418 is manually operated by a user of the catheter 102. In at least embodiments, the shut-off valve 418 operates in response to one or more specific conditions (e.g., an unsafe pressure level within the lumen, or the like) via a sensor (e.g., a pressure sensor, or the like).

In at least some embodiments, the hub 204 further includes a seal 420 through which the connector shaft 404 extends. In at least some embodiments, the seal 420 prevents the acoustically-favorable medium from entering at least a portion of at least one of the hub 204 or the control module 104 from the lumen 304. In at least some embodiments, the seal 420 is static, while the connector shaft 404 is rotatable. In at least some embodiments, the seal 420 forms a proximal end of the lumen 304.

Figure 5A:
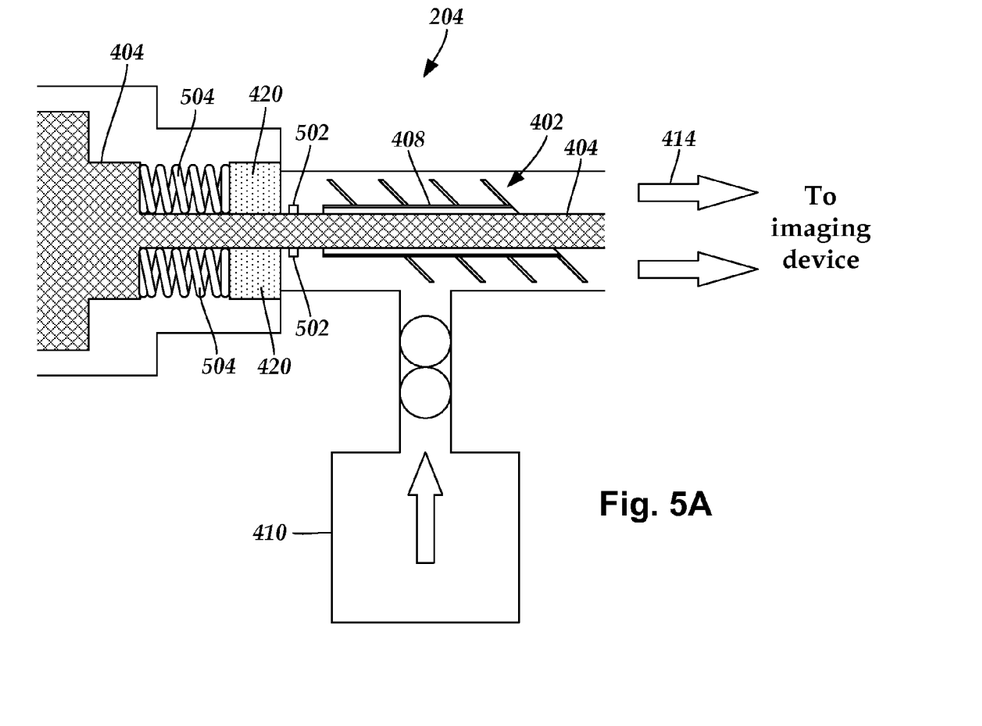
FIG. 5A is a schematic longitudinal cross-sectional view of another embodiment of a pumping apparatus disposed over a portion of a rotatable connector shaft in a hub of a catheter, the pumping apparatus in a disengaged position such that the pumping apparatus does not rotate with the connector shaft, according to the invention.
Figure 5B:
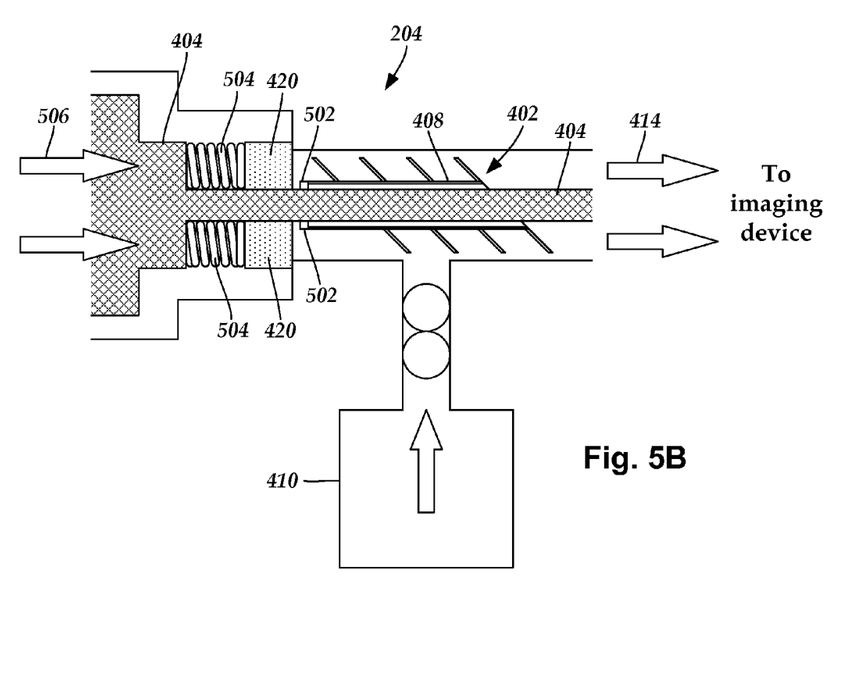
FIG. 5B is a schematic longitudinal cross-sectional view of one embodiment of the pumping apparatus of FIG. 5A, the pumping apparatus in an engaged position such that the pumping apparatus rotates with the connector shaft, according to the invention.

Turning to FIGS. 5A and 5B, in at least some embodiments the pumping apparatus 402 is configured and arranged such that the pumping apparatus 402 may transition between an engaged position (where the pumping apparatus 402 rotates with the connector shaft 404) and a disengaged position (where the pumping apparatus 402 does not rotate with the connector shaft 404). In at least some embodiments, a user of the catheter 102 may control transitions back and forth between an engaged position and a disengaged position. In at least some embodiments, the pumping apparatus 402 remains in a disengaged position until a user transitions the pumping apparatus 402 to an engaged position.

In at least some embodiments, an engagement mechanism is used to transition the pumping mechanism 402 to an engaged position. In at least some embodiments, the engagement mechanism includes one or more locking elements and one or more expansion elements that operate to couple or uncouple the pumping apparatus 402 to or from the connector shaft 404.

FIGS. 5A and 5B are schematic longitudinal cross-sectional views of another embodiment of a pumping apparatus 402 disposed in the hub 204 of the catheter 102 such that the pumping apparatus 402 maintains a disengaged (i.e., non-rotating) position unless transitioned to an engaged (i.e., rotating) position. In FIG. 5A, the pumping apparatus 402 is shown in a disengaged position. In FIG. 5B, the pumping apparatus 402 is shown transitioned to an engaged position.

One or more locking elements 502 are disposed on the connector shaft 404. The one or more locking elements 502 rotate with the connector shaft 404. The one or more locking elements 502 are configured and arranged for coupling to the pumping apparatus 402, thereby coupling the pumping apparatus 402 to the connector shaft 404.

In at least some embodiments, the pumping apparatus 402 is disposed at least partially around a portion of the connector shaft 404. In at least some embodiments, the axle 408 of the pumping apparatus 402 is disposed at least partially around a portion of the connector shaft 404. In at least some embodiments, the pumping apparatus 402 does not rotate with the connector shaft 404, unless the pumping apparatus 402 is coupled to the one or more locking elements 502.

In at least some embodiments, the one or more locking elements 502 are disposed on a portion of the connector shaft 404 distal to the seal 420. In at least some embodiments, the one or more locking elements 502 are disposed in the lumen 304. In at least some embodiments, when the one or more locking elements 502 are not coupled to the pumping apparatus, the one or more locking elements 502 are disposed in proximity to the pumping apparatus 402. In at least some embodiments, when the one or more locking elements 502 are not coupled to the pumping apparatus, the one or more locking elements 502 are disposed proximal to the pumping apparatus 402.

Figure 6A:
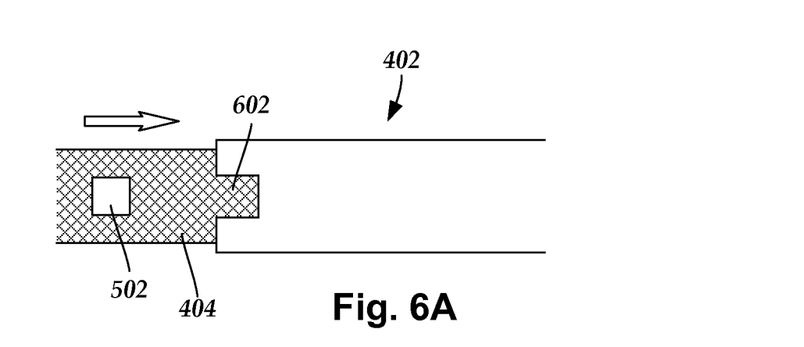
FIG. 6A is a schematic top view of one embodiment of a locking element disposed on a connector shaft and a portion of a pumping apparatus disposed over the connector shaft, the pumping apparatus defining a notch in proximity to the locking element, according to the invention.
Figure 6B:
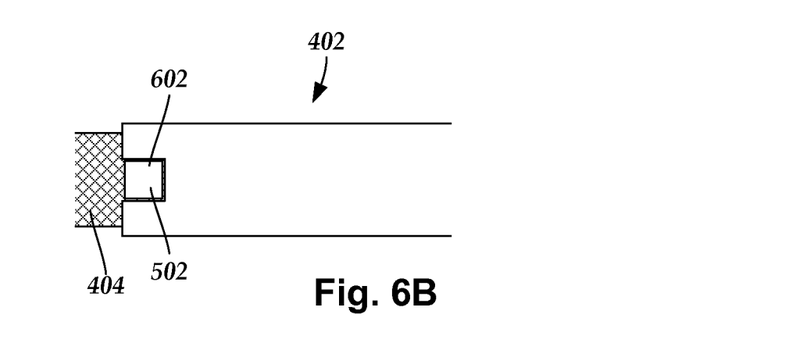
FIG. 6B is a schematic top view of one embodiment of connector shaft of FIG. 6A moved axially with respect to the pumping apparatus of FIG. 6A such that the locking element disposed on the connector shaft is inserted into the notch defined in the pumping apparatus, according to the invention.

The one or more locking elements 502 may couple and uncouple with the pumping apparatus 402 in many different ways. In at least some embodiments, the connector shaft 404 can be moved axially with respect to the pumping apparatus 402. In at least some embodiments, (as shown in FIGS. 6A and 6B) the axial movement enables the one or more locking elements 502 to insert into one or more notches 602 defined in the pumping apparatus 402. In at least some embodiments, when the one or more locking elements 502 are inserted into the one or more notches 602, rotation of the connector shaft 404 causes a corresponding rotation of pumping apparatus 402.

In at least some embodiments, axial movement of the connector shaft is controlled by one or more expansion elements 504. In at least some embodiments, the one or more expansion elements 504 are springs. In at least some embodiments, the one or more expansion elements 504 are coupled to the connector shaft 404. In at least some embodiments, the one or more expansion elements 504 are coupled to the connector shaft 404 proximal to the seal 420. In at least some embodiments, the one or more expansion elements 504 couple the connector shaft 404 to the hub 204. In at least some embodiments, the one or more expansion elements 504 couple the connector shaft 404 to the seal 420.

In at least some embodiments, when the one or more expansion elements 504 are in a relaxed state, the pumping apparatus 402 is in a disengaged position, as shown in FIG. 5A. In at least some embodiments, at least one of expansion or compression of the one or more expansion elements 504 causes a corresponding axial movement of the connector shaft 404 along a longitudinal axis of the lumen 304, thereby causing a relative movement of the one or more locking elements 504 with respect to the pumping apparatus 402. In at least some embodiments, the pumping apparatus 402 and the one or more locking elements 504 couple when the one or more expansion elements 504 are expanded. In at least some embodiments, the pumping apparatus 402 and the one or more locking elements 504 couple when the one or more expansion elements 504 are compressed, as shown in FIG. 5B.

In at least some embodiments, an applied force (shown in FIG. 5B as arrows 506) may be used to compress the one or more expansion elements 504 enough for the one or more locking elements 502 to engage with the pumping apparatus 502. In at least some embodiments, compression of the one or more expansion elements 504 is implemented manually, for example, by pulling a lever coupled to the one or more expansion elements 504. In at least some embodiments, compression of the one or more expansion elements 504 is implemented automatically, for example, via the drive unit 110.

In at least some embodiments, the lumen 304 is at least partially filled with the acoustically-favorable medium and sealed prior to use. In at least some embodiments, the lumen 304 is at least partially filled with the acoustically-favorable medium prior to an imaging procedure such that the pumping apparatus 402 remains in contact with at least some of the acoustically-favorable medium. In at least some embodiments, the lumen 304 is at least partially filled with the acoustically-favorable medium during an imaging procedure such that the pumping apparatus 402 remains in contact with at least some of the acoustically-favorable medium.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A catheter assembly for an intravascular ultrasound system, the catheter assembly comprising:
    an elongated catheter having a distal end and a proximal end, the catheter defining a lumen extending along the catheter from the proximal end to the distal end, the catheter comprising a hub disposed at the proximal end of the catheter, the hub comprising a rotatable connector shaft disposed at least partially in the lumen;
    a pumping apparatus coupled to the connector shaft such that rotation of the connector shaft causes a corresponding rotation of the pumping apparatus;
    a reservoir in fluid communication with the pumping apparatus, the reservoir configured and arranged for inputting an acoustically-favorable medium to the pumping apparatus; and
    an imaging core configured and arranged for inserting into the lumen, the imaging core comprising an imaging device coupled to a distal end of an elongated, rotatable drive member, the imaging device comprising at least one transducer mounted to the imaging device, the at least one transducer configured and arranged for transforming applied electrical signals to acoustic signals and also for transforming received echo signals to electrical signals;
    wherein the rotatable connector shaft is coupled to a proximal end of the drive member such that rotation of the connector shaft causes a corresponding rotation of the imaging core.

2. The catheter assembly of claim 1, wherein the pumping apparatus comprises a screw pump.

3. The catheter assembly of claim 1, wherein the hub further comprises a seal through which the connector shaft extends, the seal preventing the acoustically-favorable medium from entering at least a portion of the hub when the acoustically-favorable medium is disposed in the lumen.

4. The catheter assembly of claim 1, further comprising at least one check valve disposed between the lumen and the reservoir.

5. The catheter assembly of claim 4, further comprising a shut-off valve between the at least one check valve and the reservoir.

6. The catheter assembly of claim 1, further comprising a drive unit coupled to the connector shaft, the drive unit configured and arranged for controlling rotation of the connector shaft.

7. The catheter assembly of claim 1, further comprising a control module coupled to the drive unit, the control module comprising
    a pulse generator electrically coupled to the imaging core, the pulse generator configured and arranged for providing electric signals to the imaging core, and
    a processor electrically coupled to the imaging core, the processor configured and arranged for processing received electrical signals from the imaging core to form at least one image.

8. The catheter assembly of claim 1, wherein the catheter defines an output port in fluid communication with the lumen, the output port configured and arranged for flushing out gas from the lumen.

9. A catheter assembly for an intravascular ultrasound system, the catheter assembly comprising:
    an elongated catheter having a distal end and a proximal end, the catheter defining a lumen extending along the catheter from the proximal end to the distal end, the catheter comprising a hub disposed at the proximal end of the catheter, the hub comprising a rotatable connector shaft at least partially disposed in the lumen;
    a pumping apparatus coupleable to the connector shaft, wherein rotation of the connector shaft causes a corresponding rotation of the pumping apparatus when the pumping apparatus is coupled to the connector shaft;
    a reservoir in fluid communication with the pumping apparatus, the reservoir configured and arranged for inputting an acoustically-favorable medium to the pumping apparatus; and
    an imaging core configured and arranged for inserting into the lumen, the imaging core comprising an imaging device coupled to a distal end of an elongated, rotatable drive member, the imaging device comprising at least one transducer mounted to the imaging device, the at least one transducer configured and arranged for transforming applied electrical signals to acoustic signals and also for transforming received echo signals to electrical signals;
    wherein the rotatable connector shaft is coupled to a proximal end of the drive member such that rotation of the connector shaft causes a corresponding rotation of the imaging core.

10. The catheter assembly of claim 9, wherein the connector shaft comprises at least one locking element.

11. The catheter assembly of claim 10, wherein the hub further comprises at least one expansion element coupled to the connector shaft.

12. The catheter assembly of claim 11, wherein the at least one expansion element is coupled to the connector shaft such that expansion or compression of the at least one expansion element causes an axial movement of the at least one locking element with respect to the pumping apparatus.

13. The catheter assembly of claim 12, wherein the pumping apparatus is configured and arranged to couple to the connector shaft when the at least one expansion element is compressed with enough force to cause the at least one locking member to couple to the pumping apparatus.

14. A method for flushing air from a catheter of an intravascular ultrasound imaging system, the method comprising:
    inserting a distal end of a catheter into a patient, the catheter defining a lumen extending along the catheter from a proximal end to a distal end, the catheter comprising a hub disposed at the proximal end of the catheter, the hub comprising a rotatable connector shaft disposed in the lumen and a pumping apparatus;
    inserting an imaging core into the lumen, the imaging core comprising an imaging device coupled to a distal end of an elongated, rotatable drive member, the imaging device comprising at least one transducer mounted to the imaging device, the drive member coupled to the connector shaft;
    providing acoustically-favorable medium to the pumping apparatus from a reservoir in fluid communication with the lumen;
    rotating the connector shaft to cause a corresponding rotation of the imaging core;
    coupling the pumping apparatus to the connector shaft to cause the pumping apparatus to rotate with the connector shaft; and pumping the acoustically-favorable medium from the hub to the imaging device using the pumping apparatus.

15. The method of claim 14, wherein the pumping apparatus comprises a screw pump.

16. The method of claim 14, wherein coupling the pumping apparatus to the connector shaft to cause the pumping apparatus to rotate with the connector shaft comprises compressing an expansion element within the hub with enough force to cause at least one locking element disposed on the connector shaft to move axially a sufficient distance along a longitudinal axis of the lumen to couple the at least one locking element to the pumping apparatus.

17. The method of claim 14, wherein providing acoustically-favorable medium to the pumping apparatus from a reservoir in fluid communication with the lumen comprises providing acoustically-favorable medium from the reservoir to the pumping apparatus such that the acoustically-favorable medium maintains contact with the pumping apparatus.

18. The method of claim 14, wherein providing acoustically-favorable medium to the pumping apparatus from a reservoir in fluid communication with the lumen comprises providing the acoustically-favorable medium through at least one check valve.

19. The method of claim 14, further comprising uncoupling the pumping apparatus from the connector shaft to cause the pumping apparatus to cease rotating with the connector shaft.

20. The method of claim 14, further comprising removing air from the lumen through an output port defined in the catheter.

* * * * *